United States Patent [19]

Carberry et al.

[11] Patent Number: 5,078,596
[45] Date of Patent: Jan. 7, 1992

[54] ORTHODONTIC BRACKET AND ASSOCIATED FABRICATING METHOD

[75] Inventors: John J. Carberry, Greene County; John A. Negrych, Jefferson County, both of Tenn.

[73] Assignee: Minco, Inc., Midway, Tenn.

[21] Appl. No.: 538,300

[22] Filed: Jun. 14, 1990

[51] Int. Cl.⁵ ............................................. A61C 3/00
[52] U.S. Cl. ........................................... 433/8; 433/9
[58] Field of Search ......................... 433/8, 9, 10, 24

[56] References Cited

U.S. PATENT DOCUMENTS

| | | | |
|---|---|---|---|
| 4,180,912 | 1/1980 | Kesling | 433/13 |
| 4,302,532 | 11/1981 | Wallshein | 433/8 |
| 4,681,538 | 6/1987 | DeLuca et al. | 433/9 |
| 4,894,012 | 1/1990 | Goldberg | 433/215 |
| 4,936,773 | 6/1990 | Kawaguchi | 433/9 |
| 4,988,293 | 1/1991 | Collins et al. | 433/8 |

Primary Examiner—John J. Wilson
Assistant Examiner—Cindy A. Cherichetti
Attorney, Agent, or Firm—Pitts and Brittian

[57] ABSTRACT

An orthodontic bracket for securing orthodontic appliances to a tooth and an associated fabricating method. The orthodontic bracket (10) generally comprises a body (18) fabricated of a high strength plastic material (22) filled with an oxide particulate filler (24). In certain alternate embodiments the body (18) is further strengthened by dispersing reinforcing fibers (32) in the plastic material (22). The body (18) in certain embodiments is coated with a layer of organo-functional silane (28) and/or a high strength plastic (30) so as to resist staining and/or abrasion. The method of the present invention generally comprises filling the plastic fabricating material (22) with the oxide filler (28) and/or reinforcing fibers and/or whiskers (32) and molding the composite material into the desired bracket body configuration. The body (18) can then be coated with the desired protective abrasion and stain resistant coating (30).

45 Claims, 4 Drawing Sheets

ORTHODONTIC BRACKET AND ASSOCIATED FABRICATING METHOD

TECHNICAL FIELD

This invention relates to an orthodontic bracket for securing an arch wire or other orthodontic appliances to the tooth of a patient, and an associated bracket fabricating method. In this particular invention the bracket generally comprises a body fabricated of a high strength polymer (plastic), preferably, filled with a colloidal oxide filler, fibers and/or whiskers.

BACKGROUND ART

In the orthodontic art, it is a common practice to place metal, plastic or ceramic brackets upon the teeth in order that an arch wire can be stretched across these brackets for the purpose of properly positioning the teeth. These brackets must have the strength to withstand high pressure when wires are stretched across them. However, the bracket's composition must be susceptible to mechanical (or chemical) bonding to the tooth. Another aspect which must be considered is the aesthetic durability of the bracket.

The original orthodontic brackets were based on metal bands, which were wrapped around the tooth. These were extremely unaesthetic and presented difficulty in the mechanics of moving the tooth into proper position. In addition, these orthodontic appliances were extremely labor intensive and often caused damage to the tooth due to difficulty (or impossibility) of maintaining proper dental hygiene.

A second generation of orthodontic brackets were based on a smaller metal bracket which could be affixed directly to the face of the tooth. These brackets were affixed by mechanical bonding between the etched enamel of the tooth and the interlocking grid structure on the bonding surface of the bracket. While more aesthetic than bands, these metal brackets were still quite unaesthetic. Also, these metal brackets could be difficult to bond to the tooth due to the need to entirely fill the grid structure of the bonding surface of the bracket with adhesive. In addition, these metal brackets were expensive to manufacture due to the complexity of the manufacturing process.

A third generation of orthodontic brackets was the lingual device which was affixed to the back side of the tooth. While this method was more aesthetic than previous ones, it presented difficulties in bonding and practice.

A fourth generation of orthodontic brackets was the plastic bracket. While being moderately aesthetic and inexpensive, these brackets would stain and thereby depreciate the aesthetic quality of the brackets. In addition, the plastic composition did not provide adequate stiffness and often resulted in the plastic bracket detaching from the tooth due to the inability of the bracket to hold the adhesive in place. Also, due to its lack of stiffness, treatment was restricted to cases requiring minimal mechanical treatment.

A fifth generation of orthodontic devices was the ceramic bracket. While this bracket was translucent and thereby very aesthetic, the ceramic composition produced a brittle structure. This bracket was also very abrasive to opposing and impinging teeth as well as the arch wire. In addition, the ceramic bracket was difficult to remove, often resulting in damage to the tooth enamel.

Certain related devices, compositions, and methods are disclosed in U.S. Pat. Nos. 3,895,445; 4,435,160; 4,695,251; and 4,772,325.

Accordingly, it is an object of the present invention to provide a plastic/composite orthodontic bracket which is essentially color neutral and thereby aesthetic due to the transparent (or translucent) properties of the constituents.

It is also an object of the present invention to provide an orthodontic bracket which will not stain, even with exposure to foods and drinks, including coffee, cigarettes, juices, etc.

It is a further object of the invention to provide an orthodontic bracket which is chemically bondable to an etched tooth or enamel surface using standard orthodontic adhesives which are designed to chemically adhere to an etched tooth or enamel surface.

It is a further object of the invention to provide an orthodontic bracket which is stiffer and stronger than other plastic brackets.

It is yet another object of the invention to provide an orthodontic bracket which is both tough with respect to the mechanical stresses and wear of the arch wire dynamics and also non-abrasive when in contact with adjacent and/or impinging teeth.

It is a further object of the invention to provide an orthodontic bracket which is formed by injection or compression molding and is curable by heat, chemical reaction or microwave or other electro-magnetic radiation.

Yet another object of the present invention is to provide an orthodontic bracket which is inexpensive to manufacture.

DISCLOSURE OF THE INVENTION

Other object and advantages will be accomplished by the present invention which provides an orthodontic bracket for securing orthodontic appliances to a tooth, and an associated bracket fabricating method. The orthodontic bracket comprises a bracket body made of a high strength, thermal, chemical or electromagnetic radiation cured polymer containing organic or inorganic fillers typically being, but not limited to colloidal oxides and inorganic fibers and/or whiskers to add strength and stiffness to the body. The body can also be coated with a protective coating to resist staining and/or abrasion. In various embodiments of the inventions, the coating includes an organo-functional silane layer and/or a high strength plastic stain and abrasion resistant coating. Generally, the method of the present invention includes the steps of filling the plastic fabricating material with the oxide filler and/or reinforcing fibers or whiskers, and then molding the bracket into the desired configuration. The body can then be cured using heat, chemical reactions or electro-magnetic radiation. The cured bracket can then be coated with an organo-functional silane or coated with an abrasion and stain resistant coating.

BRIEF DESCRIPTION OF THE DRAWINGS

The above mentioned features of the invention will become clearly understood from the following detailed description of the invention read together with the drawings in which.

BEST MODE FOR CARRYING OUT THE INVENTION

Figure 1:
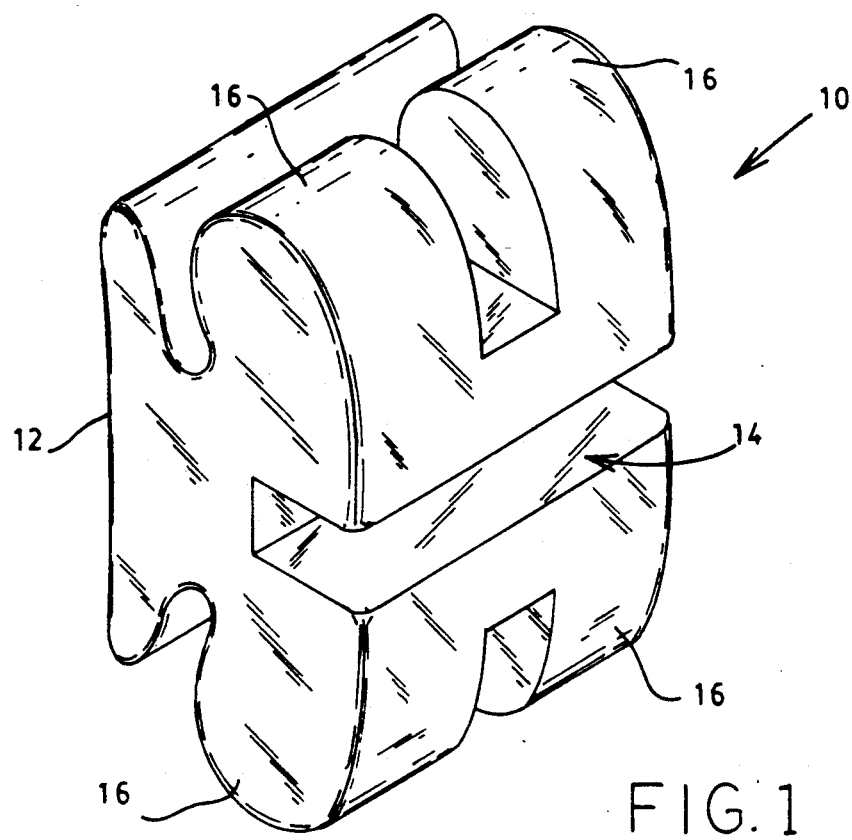
FIG. 1 illustrates a perspective view of an orthodontic bracket of the present invention.

An orthodontic bracket incorporating various features of the present invention is illustrated generally at 10 in FIG. 1. As will be understood by those skilled in the art, the bracket 10 is used for securing an arch wire to the tooth of a patient, the arch wire serving to selectively apply pressure to the tooth to move the tooth to a desired position. Accordingly, the bracket 10 defines a rearward tooth engaging surface 12 and is provided with a forwardly disposed arch wire slot 14 for receiving an arch wire (not shown). Whereas the configuration of the bracket 10 can vary depending upon the particular application, in one embodiment the bracket 10 includes the wing portions 16 which serve as means for attaching elastic bands for purposes of ligation and attachment of other devices as deemed necessary by the orthodontist.

For aesthetic purposes the bracket 10 is preferably translucent, e.g. with 30%–40% visible light transmission, such that the bracket 10 transmits the coloration of the tooth on which it is secured, without the artificial reflectivity of total transparency. However, it will be understood that, if desired, the bracket 10 can be constructed so as to be totally transparent or can be pigmented to match the coloration of the operatively associated tooth.

Figure 2:
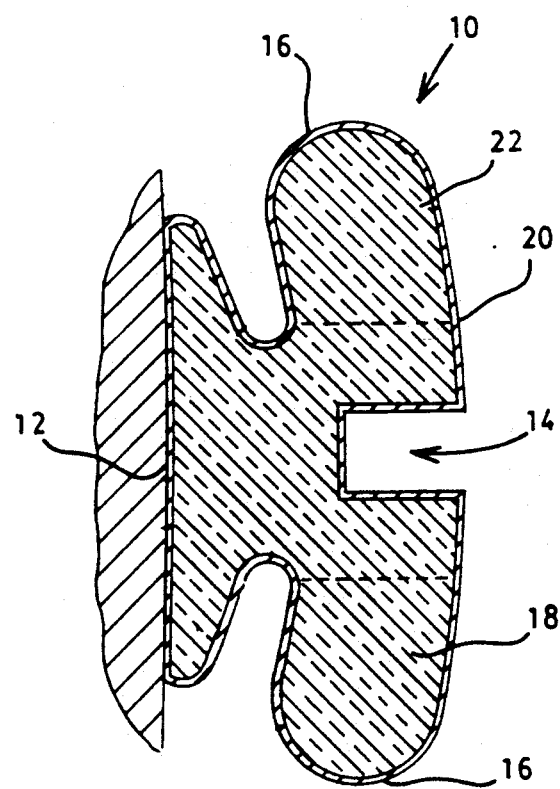
FIG. 2 illustrates a side elevation view, in section, of an orthodontic bracket of the present invention.

As illustrated in FIG. 2, the bracket 10 generally comprises a body 18 which is preferably, coated with a stain and/or abrasion resistant coating 20. In the embodiment of FIG. 2, the body 18 is fabricated of a plastic material 22 such as a high strength polycarbonate. One suitable material is the high strength plastic, Lexan. Utilizing such material, the body can be formed by injection or compression molding, or other suitable molding processes as will be discussed further below.

Figure 3:
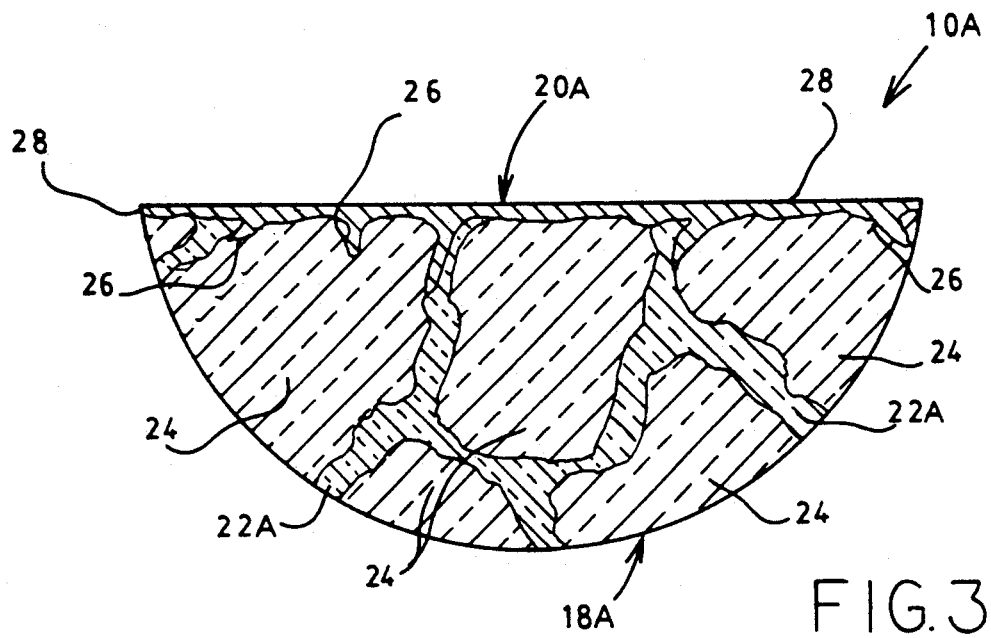
FIG. 3 illustrates a partial side view, in section, of one alternate embodiment of an orthodontic bracket of the present invention diagrammatically depicting the composition of such bracket.
Figure 4:
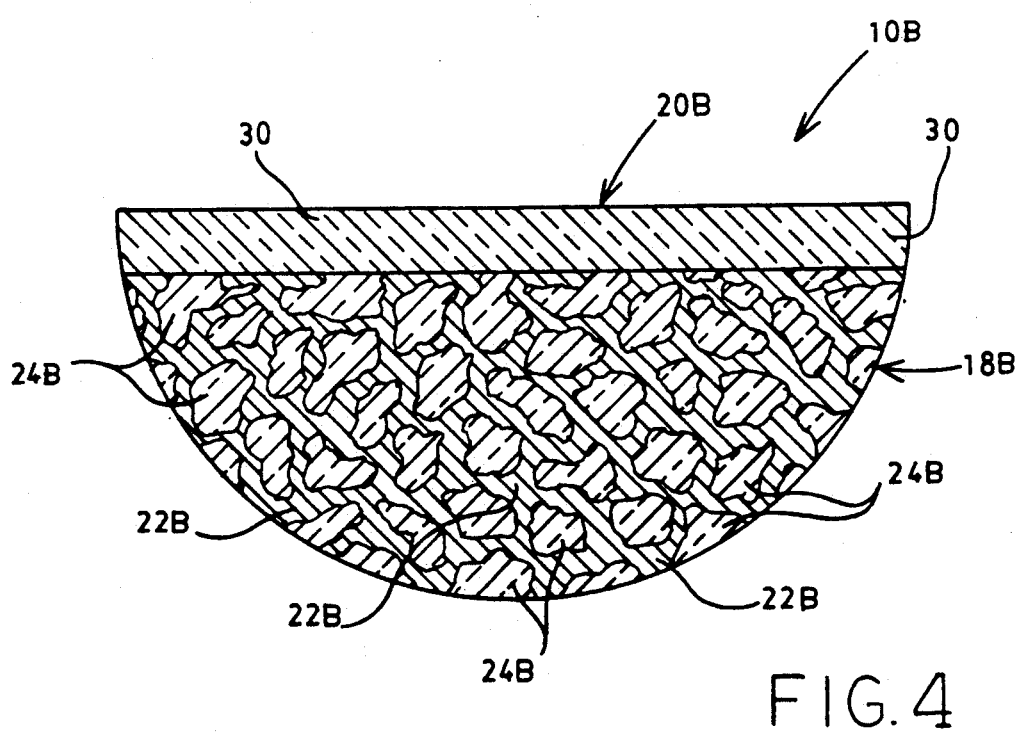
FIG. 4 illustrates a partial side view, in section, of one alternate embodiment of an orthodontic bracket of the present invention diagrammatically depicting the composition of such bracket.

As diagrammatically depicted at 18A in FIG. 3 and 4, in an alternate embodiment the body of the bracket 10 is strengthened and made more rigid by dispersing a particulate oxide filler 24 in the plastic fabricating material 22A. Suitable oxide fillers include, without limitation, alumina ($Al_2O_3$), silica, aluminum hydroxide, wollastonite, spinel, and mixtures, thereof. Further, the oxide filler 28 preferably defines sub-micron, colloidal-sized oxides in order to facilitate the compacting of the filler within the resulting matrix, and, thus, reduce irregularities in, and the porosity of, the exterior surface of the body 18A. By reducing the irregularities in, and the porosity of, the exterior surface, the surface is less susceptible to staining.

The concentration of the colloidal oxide filler 28 within the matrix can vary depending upon the strength and rigidity desired. Further, in the preferred embodiment the filler 24 is translucent for purposes of aesthetics, but the light transmitting capacity of the filler can vary as desired. In this regard, it will be recognized that the resulting light transmitting capacity of the body 18A will vary depending upon the light transmitting capacity of the filler 24 and the density of the filler 24 within the polycarbonate matrix. Thus, for example, where a transparent plastic is used for the material 22, the desired translucence of the body 18A can be obtained through use of a filler 24 having a preselected, lesser light transmission capacity at a preselected density.

As noted above, the colloidal oxide filler 24 is readily compactible so as to reduce the porosity of the exterior surface of the body of the bracket. However, whenever a filler is used in a plastic small pores or capillaries such as those illustrated at 26 in FIG. 3 can form in the exterior surface. If unfilled, these capillaries can fill with foreign matter, resulting in the staining of the exterior surface of the bracket 10. In order to obviate such staining, in the embodiment of FIG. 3, the coating 20A includes a coating of organo-functional silane 28. As illustrated, the silane coating fills the pores and capillaries 26 of the exterior surface of the body 18A and provides a smooth surface which resists staining. The silane coating 28 can be applied, as by dipping, spraying or painting.

Referring now to FIG. 4, in an alternate embodiment the coating 20B comprises a high strength stain and abrasion resistant plastic coating 30, bonded to the body 18B. Particularly suited for this purpose is a silicone or acrylic material which is curable with ultraviolet or other electro-magnetic radiation, by solvent evaporation (drying) or by heat. The plastic coating 30 can be applied to the body 18B by dipping, painting or spraying and serves to provide a smooth abrasion and stain resistant exterior surface.

Figure 5:
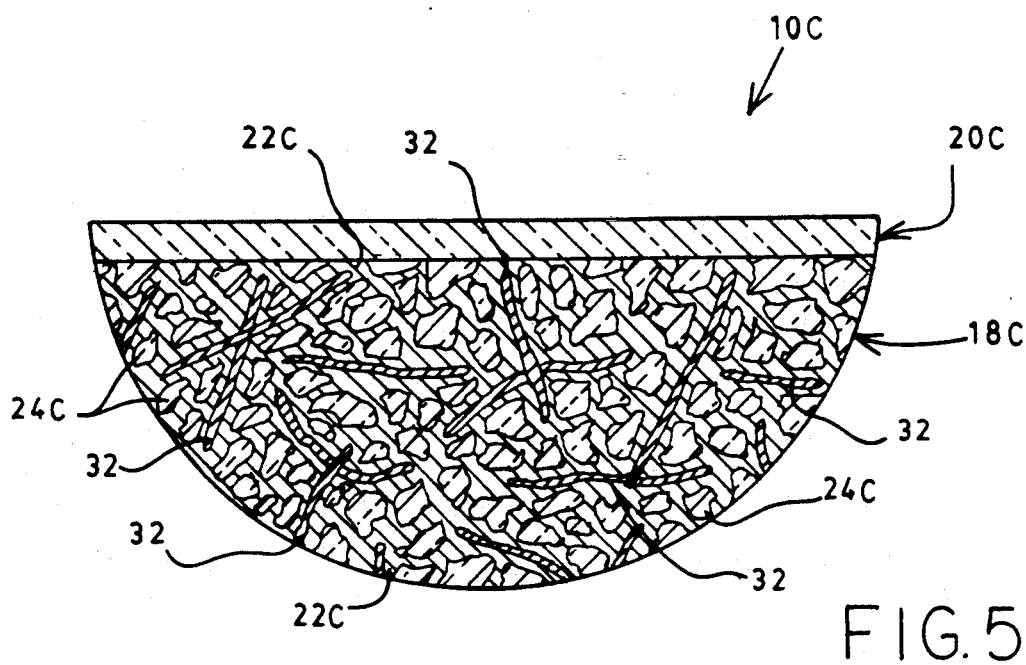
FIG. 5 illustrates a partial side view, in section, of one alternate embodiment of an orthodontic bracket of the present invention diagrammatically depicting the composition of such bracket.
Figure 6:
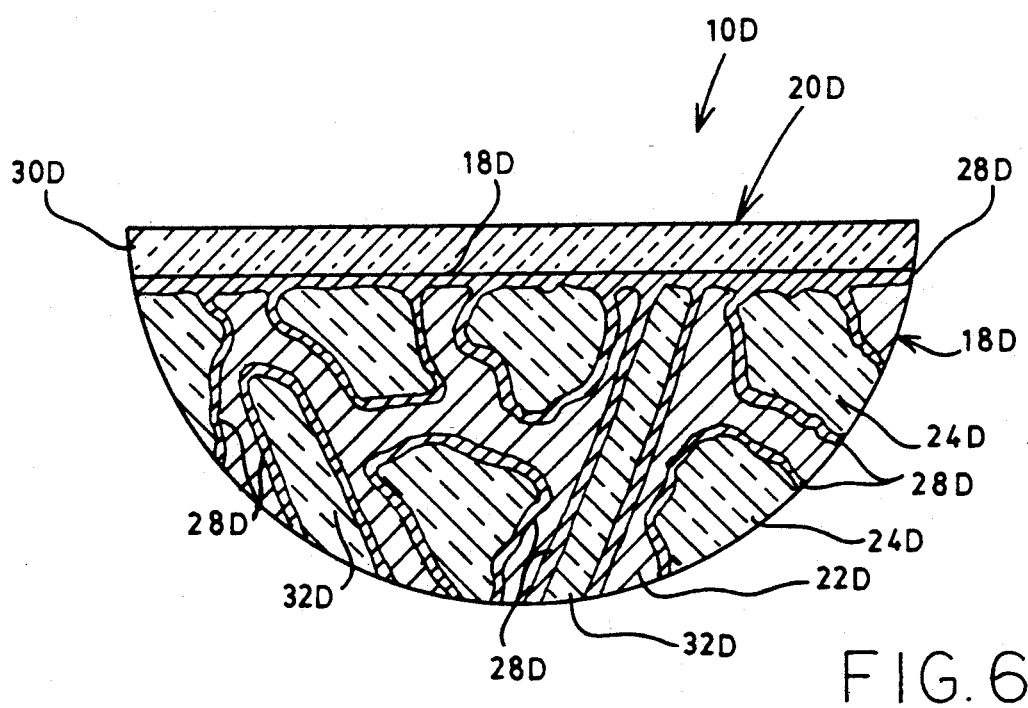
FIG. 6 illustrates a partial side view, in section, of one alternate embodiment of an orthodontic bracket of the present invention diagrammatically depicting the composition of such bracket.

In the further alternate embodiment illustrated in FIG. 5 it will be noted that the body 18C can also be strengthened by dispersing reinforcing whiskers or fibers 32 in the polycarbonate material 22C. Preferably the fibers 32 are fabricated of glass or ceramic and are translucent. Of course, the fibers 32 can be used without the oxide filler 24C. However, the combination of a colloidal oxide filler 24C and fibers 32 in this matrix is particularly effective in providing a strong durable bracket. In this regard, the colloidal-sized oxides 24C serve to efficiently fill the spaces between the fibers or whiskers 32 firmly locking the fibers 32 in the matrix. Further, organo-functional silanes function as adhesion promoters and can be engineered to have affinities for differing materials so as to aid in the bonding together of such materials. Thus, as illustrated in the preferred embodiment of FIG. 6, the particles of the oxide filler 24D and the fibers or whiskers 32D can be coated with organo-functional silanes 28D to promote the bonding of the filler 24D and the fibers or whiskers 32D with the polycarbonate material 22D. The body 18D can be coated with the abrasion and stain resistant coating 30D. It is also possible to coat the body 18D with the silane 28D and give it a level of stain resistance by sealing the surface. In this case the abrasion and stain resistant coating 30D would not be used.

Figure 7:
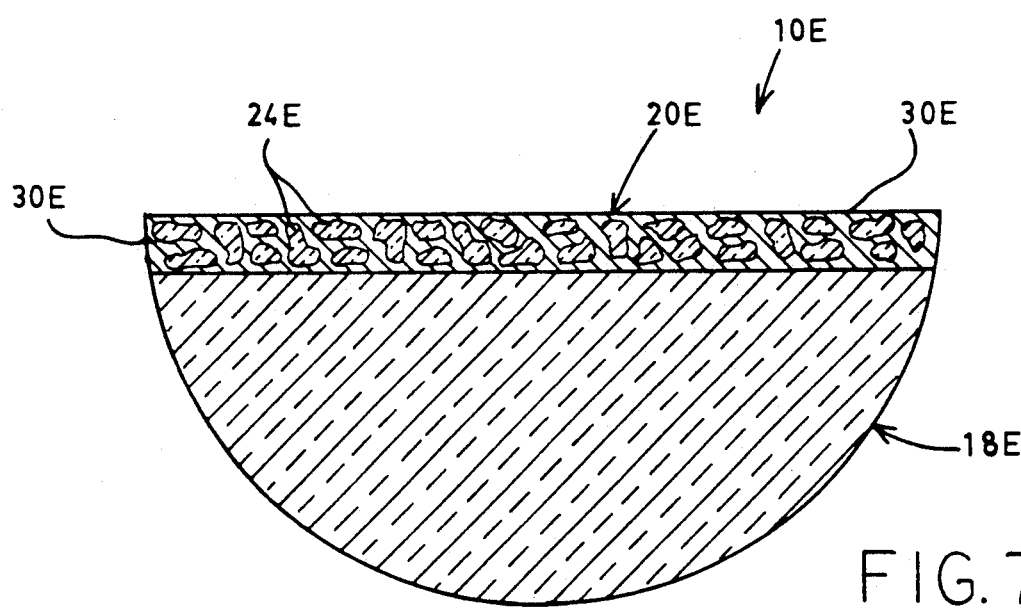
FIG. 7 illustrates a partial side view, in section, of one alternate embodiment of an orthodontic bracket of the present invention diagrammatically depicting the composition of such bracket.

With respect to FIG. 7, in this embodiment the stain and abrasion resistant coating 30E has been filled with a colloidal oxide filler 24E to strengthen and control translucence of the coating 30E. Of course, the filler 24E can be coated with silane prior to dispersal in the coating and applied to the exterior surface of the body to promote bonding with the coating material. Further, it will be recognized that the filled coating 30E of FIG. 7 can be utilized with an oxide and/or fiber or whisker filled body as discussed above, if desired.

In view of the above, it will be understood by those skilled in the art that the present invention provides an aesthetically desirable, stain and abrasion resistant orthodontic bracket with great advantages over the prior art. Moreover, the bracket can be manufactured cost efficiently. For example, to produce one preferred embodiment, the filler 24 and/or fibers or whiskers 32 are coated with an organo-functional silane 28, and the coated filler 24 and/or fibers or whiskers 32 are dispersed in the plastic matrix material 22 to produce the desired composite material for fabrication of the body 18. Then, utilizing the composite material, the body is formed by injection or compression molding, and the stain and abrasion resistant coating 30 is then applied to the body 18. Of course, as discussed above the coating 30 can be filled with colloidal oxides if desired.

The bracket 10 is chemically bondable to an etched tooth or enamel surface using standard orthodontic adhesives due to the coating of silanes 28 which have a high level of adhesion to the bracket bonding surface due to the presence of silanes, colloidal oxides and inorganic fibers or whiskers which may be silanated or unsilanated themselves. In this regard, as illustrated in FIG. 2, a coating of organo-functional silane 28 can be applied to the tooth engaging surface 12 of the bracket 10 to promote adhesion of the bracket 10 to the tooth. The particular silane utilized will be specific to the adhesive to be used to secure the bracket 10 and specific to the material defining the tooth engaging surface 12.

While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. An improved orthodontic bracket for engaging a tooth to facilitate the securing of orthodontic appliances to said tooth, said bracket comprising a body fabricated of a high-strength polycarbonate with a colloidal oxide filler selected from a group consisting of alumina, silica, aluminum hydroxide, wollastonite, mullite, spinel and mixtures thereof and fibers/whiskers dispersed therein thereby imparting strength, wherein said polycarbonate is capable of transmitting light and wherein said body further comprises a thin protective coating wherein said protective coating is stain and abrasion resistant and is capable of transmitting light thereby increasing the aesthetic quality of said orthodontic bracket and wherein particles of said colloidal oxide filler are coated with an organo-functional silane to promote bonding between said particles and said polycarbonate.

2. The orthodontic bracket of claim 1 wherein said colloidal oxide filler is selected from a group consisting of alumina, silica, aluminum hydroxide, wollastonite, mullite, spinel and mixtures thereof.

3. The orthodontic bracket of claim 1 wherein said fibers/whiskers are coated with an organo-functional silane to promote bonding between said fibers/whiskers and said polycarbonate.

4. The orthodontic bracket of claim 3 wherein said body defines a tooth engaging surface coated with an organo-functional silane, whereby a conventional orthodontic adhesive can be used to chemically bond said tooth engaging surface to said tooth whereby said silanes, said colloidal oxides and said fibers/whiskers produce a high level of adhesion.

5. An improved orthodontic bracket for engaging a tooth to facilitate the securing of orthodontic appliances to said tooth, said bracket comprises a polymer containing curing agents, including a combination of peroxides and free radicals which can be freed for bonding by an input of electro-magnetic energy, filled with a colloidal oxide filler to form a composite fabricating material which is molded into a preselected bracket configuration to produce a bracket body and cured to increase its strength wherein reinforcing fibers/whiskers are dispersed in said polymer and wherein particles of said colloidal oxide filler and said reinforcing fibers/whiskers are coated with an organo-functional silane to enhance the bond between said particles and fibers and said polymer.

6. The orthodontic bracket of claim 5 wherein said body defines a tooth engaging surface and wherein said tooth-engaging surface is coated with an organo-functional silane to promote adhesion of said bracket to a tooth.

7. The orthodontic bracket of claim 6 wherein said tooth-engaging surface is chemically bonded to said tooth using a conventional orthodontic adhesive, whereby said coating of silane on said tooth-engaging surface and the presence of said silanes, said colloidal oxides and said fibers/whiskers produces a high level of adhesion.

8. The orthodontic bracket of claim 5 wherein said bracket is molded by injection molding.

9. The orthodontic bracket of claim 5 wherein said body of said bracket is coated with an organo-functional silane coating wherein said organo-functional silane is applied by means selected from a group consisting of dipping, spraying and painting.

10. The orthodontic bracket of claim 5 wherein said body of said bracket is coated with a stain and abrasion resistant plastic coating wherein said stain and abrasion resistant plastic coating is applied by means selected from a group consisting of dipping, spraying and painting.

11. The orthodontic bracket of claim 5 wherein said body defines a tooth engaging surface and wherein said tooth-engaging surface is coated with an organo-functional silane to promote adhesion of said bracket to a tooth.

12. The orthodontic bracket of claim 5 wherein said fabricating material is cured with electro-magnetic radiation to enhance its strength and durability.

13. The orthodontic bracket of claim 5 wherein said fabricating material is cured with heat to enhance its strength and durability.

14. The orthodontic bracket of claim 5 wherein said fabricating material is cured by drying to enhance its strength and durability.

15. An orthodontic bracket for engaging a tooth to facilitate the securing of orthodontic appliances to said tooth, said bracket comprising a body at least partially fabricated of a high strength plastic material with a colloidal oxide filler dispersed therein thereby imparting strength wherein said plastic material is capable of transmitting light and wherein said body further comprises a thin protective coating, wherein said protective coating is stain and abrasive resistant and is capable of transmiting light thereby increasing the aesthetic quality of said orthodontic bracket and wherein particles of said colloidal oxide filler are coated with an organo-functional silane to promote bonding between said particles and said plastic material.

16. The orthodontic bracket of claim 15 wherein said plastic material comprises a polycarbonate material.

17. The orthodontic bracket of claim 15 wherein said plastic material comprises a material containing peroxides and free radicals which is curable with electromagnetic radiation to enhance its strength and durability.

18. The orthodontic bracket of claim 15 wherein said plastic material comprises a material containing peroxides and free radicals which is curable with heat to enhance its strength and durability.

19. The orthodontic bracket of claim 15 wherein said filler comprises a colloidal-sized oxide particulate selected from the group consisting of alumina, silica, aluminum hydroxide, wollastonite, mullite, spinel and mixtures thereof.

20. The orthodontic bracket of claim 19 wherein the particles of said colloidal oxide particulate are coated with an organo-functional silane to promote bonding between said oxide filler and said plastic material.

21. The orthodontic bracket of claim 15 wherein said body is fabricated of said plastic material with reinforcing fibers/whiskers disbursed therein.

22. The orthodontic bracket of claim 21 wherein said fibers/whiskers are coated with an organo-functional silane to promote bonding between said fibers/whiskers and said plastic material.

23. The orthodontic bracket of claim 22 wherein wherein said fibers/whiskers are fabricated of a ceramic material.

24. The orthodontic bracket of claim 21 wherein said fibers/whiskers are fabricated of glass.

25. The orthodontic bracket of claim 15 wherein said body defines a tooth engaging surface coated with an organo-functional silane to promote adhesion of said bracket to said tooth.

26. The orthodontic bracket of claim 15 wherein said thin protective coating defines a coating of organo-functional silane thereby forming a smooth surface which resists staining thereby increasing the aesthetic quality of said orthodontic bracket.

27. The orthodontic bracket of claim 26 wherein said organo-functional silane is applied by means selected from a group consisting of dipping, spraying and painting.

28. The orthodontic bracket of claim 15 wherein said thin protective coating defines a stain and abrasion resistant acrylic material curable with electro-magnetic radiation.

29. The orthodontic bracket of claim 28 wherein said acrylic material is applied by means selected from a group consisting of dipping, spraying and painting.

30. The orthodontic bracket of claim 15 wherein said thin protective coating defines a stain and abrasion resistant acrylic material curable with heat.

31. The orthodontic bracket of claim 15 wherein said thin protective coating defines a stain and abrasion resistant acrylic material curable by drying.

32. The orthodontic bracket of claim 15 wherein said thin protective coating defines a stain and abrasion resistant silicone material which is curable with electro-magnetic radiation.

33. The orthodontic bracket of claim 15 wherein said thin protective coating defines a stain and abrasion resistant silicone material which is curable with heat.

34. The orthodontic bracket of claim 15 wherein said thin protective coating defines a stain and abrasion resistant silicone material which is curable by drying.

35. The orthodontic bracket of claim 15 wherein a colloidal oxide filler is dispersed in said thin protective coating to strengthen said coating and to render it translucent.

36. A method for fabricating an orthodontic bracket for engaging a tooth to facilitate the securing of orthodontic appliances to said tooth, said method comprising the steps of:
 filling a polymer containing curing agents, including a combination of peroxides and free radicals which can be freed for bonding by an input of electro-magnetic energy, with a colloidal oxide filler to form a composite fabricating material;
 molding said composite fabricating material into a preselected bracket configuration to produce a bracket body; and
 curing said composite material of said body with electro-magnetic radiation to increase its strength.

37. The method of claim 36, and before the step of filling said polymer, wherein said method comprises the further step of coating the particles of said colloidal oxide fillers with an organo-functional silane to enhance the bond between said polymer and said filler.

38. The method of claim 36 wherein said step of filling said polymer further included dispersing reinforcing fibers/whiskers in said polymer.

39. The method of claim 38, and before the step of filling said polymer, wherein said method further comprises the step of coating the particles of said colloidal oxide filler and said reinforcing fibers/whiskers with an organo-functional silane to enhance the bond between said particles and fibers and said polymer.

40. The method of claim 39 wherein said body defines a tooth engaging surface and wherein said method comprises the further step of coating said tooth-engaging surface with an organo-functional silane to promote adhesion of said bracket to a tooth.

41. The method of claim 40 wherein said method comprises the further step of chemically bonding said tooth-engaging surface to said tooth using a conventional orthodontic adhesive, whereby said coating of silane on said tooth-engaging surface and the presence of said silane, said colloidal oxides and said fibers/whiskers produces a high level of adhesion.

42. The method of claim 36 wherein said step of molding said composite fabricating material is accomplished by injection molding said body.

43. The method of claim 36 wherein said method comprises the further step of coating said body with an organo-functional silane coating.

44. The method of claim 36 wherein said method comprises the further step of coating said body with a stain and abrasion resistant plastic coating.

45. The method of claim 36 wherein said body defines a tooth engaging surface and wherein said method comprises the further step of coating said tooth-engaging surface with an organo-functional silane to promote adhesion of said bracket to a tooth.

* * * * *